United States Patent [19]
Crain et al.

[11] Patent Number: 5,472,943
[45] Date of Patent: Dec. 5, 1995

[54] METHOD OF SIMULTANEOUSLY ENHANCING ANALGESIC POTENCY AND ATTENUATING DEPENDENCE LIABILITY CAUSED BY MORPHINE AND OTHER OPIOID AGONISTS

[75] Inventors: Stanley M. Crain, Leonia, N.J.; Ke-fei Shen, Flushing, N.Y.

[73] Assignee: Albert Einstein College of Medicine of Yeshiva University,, Bronx, N.Y.

[21] Appl. No.: 97,460

[22] Filed: Jul. 27, 1993

Related U.S. Application Data

[63] Continuation-in-part of Ser. No. 947,690, Sep. 21, 1992, abandoned.

[51] Int. Cl.$^6$ .................................................. A61K 31/44
[52] U.S. Cl. .......................... 514/12; 514/13; 514/282
[58] Field of Search .................................. 514/12, 13, 282

[56] References Cited

U.S. PATENT DOCUMENTS

| | | | |
|---|---|---|---|
| 5,075,341 | 12/1991 | Mendelson et al. | 514/282 |
| 5,317,022 | 5/1992 | Borsodi et al. | 514/282 |
| 5,321,012 | 6/1994 | Mayer et al. | 514/282 |
| 5,352,680 | 10/1994 | Pologhese et al. | 514/282 |

OTHER PUBLICATIONS

Shen and Crain, *Regulatory Peptides*, in press (1993).
Shen and Crain, *Brain Res.*, vol. 597, 74–83 (1992).
Crain and Shen, *Brain Res.*, vol. 575, 13–24 (1992).
Wang et al., *Chinese J. Pharmacol. Toxicol.*, vol. 6, pp. 36–40 (1992).
Qin, *Chinese J. Pharmacol. Toxicol.*, vol. 6 (1992).
Lange, *Toxicol. Applied Pharmacol.*, vol. 54, pp. 177–186 (1992).
Terwilinger et al., *Brain Res.*, vol. 548, pp. 100–110 (1991).
Shen et al., *Brain Res.*, vol. 559, pp. 130–138 (1991).
Crain and Shen, *Trends Pharmacol. Sci.*, vol. 11, pp. 77–81 (1990).
Fujimoto et al., *Neuropharmacol.*, vol. 29, pp. 609–617 (1990).
Shen and Crain, *Brain Res.*, vol. 531, pp. 1–7 (1990).
Shen and Crain, *Brain Res.*, vol. 491, pp. 227–242 (1989).
North, *Trends Neurosci.*, vol. 9, pp. 114–117 (1986).
Magnan et al., *Naunyn–Schmiedleberg's Arch. Pharmacol.*, vol. 319, pp. 197–205 (1982).
Lange et al., *Toxicol. Applied Pharmacol.*, vol. 54, pp. 177–186 (1980).
Bentley and Hardy, *J. Amer. Chem. Soc.*, vol. 89, pp. 3281–3286 (1967).
Bentley and Hardy, *Proc. Chem. Soc.*, p. 220 (1963).

*Primary Examiner*—James H. Reamer
*Attorney, Agent, or Firm*—Amster, Rothstein & Ebenstein

[57] ABSTRACT

This invention relates to a method of selectively enhancing the analgesic potency of morphine and other clinically used bimodally-acting opioid agonists and simultaneously attenuating development of physical dependence, tolerance and other undesirable side-effects caused by the chronic administration of said bimodally-acting opioid agonists comprising the co-administration of a bimodally-acting opioid agonist which activates inhibitory opioid receptor-mediated functions of neurons in the nociceptive (pain) pathways of the nervous system and an opioid receptor antagonist which selectively inactivates excitatory opioid receptor-mediated side-effects caused by said bimodally-acting opioid agonists. This invention further relates to a method of detoxifying and treating opiate addicts utilizing said opioid receptor antagonists, as well as to a composition comprising an excitatory opioid receptor antagonist of the invention and a bimodally-acting opioid agonist.

10 Claims, 8 Drawing Sheets

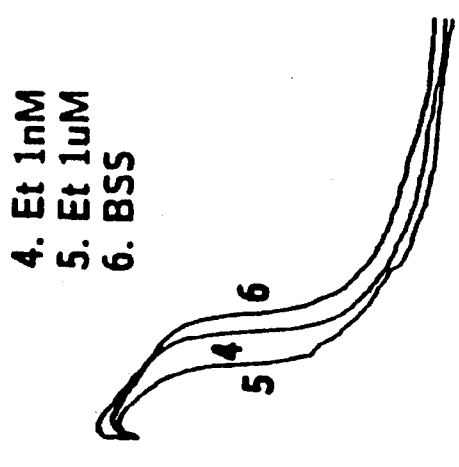
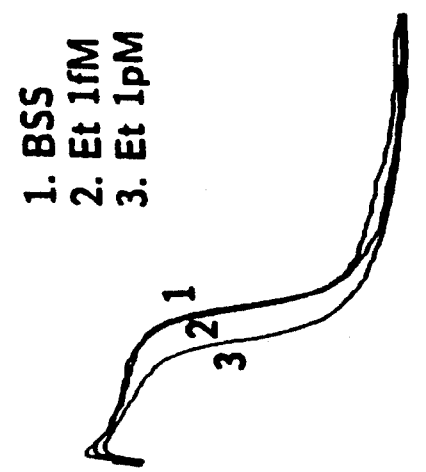
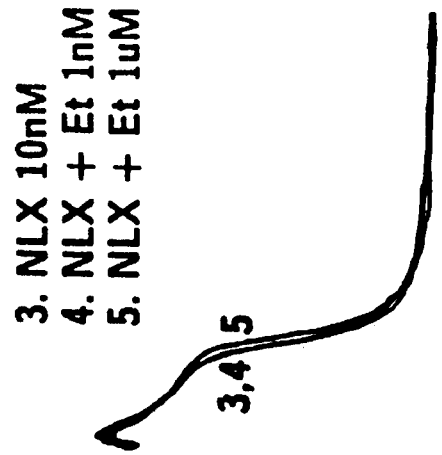
FIG. 1A
FIG. 1B

METHOD OF SIMULTANEOUSLY ENHANCING ANALGESIC POTENCY AND ATTENUATING DEPENDENCE LIABILITY CAUSED BY MORPHINE AND OTHER OPIOID AGONISTS

STATEMENT OF GOVERNMENT INTEREST

This invention was made with government support under NIDA research grant number DA 02031. As such, the government has certain rights in the invention.

CROSS-REFERENCE TO RELATED APPLICATIONS

This Application is a Continuation-In-Part of application Ser. No. 07/947,690 filed Sep. 19, 1992, now abandoned, entitled A METHOD OF IDENTIFICATION OF NON-ADDICTIVE OPIOID ANALGESICS AND THE USE OF SAID ANALGESICS FOR TREATMENT OF OPIOID ADDICTION.

FIELD OF THE INVENTION

This invention relates to a method of enhancing the analgesic (inhibitory) effects of bimodally-acting opioid agonists, including morphine and other clinically used opioid analgesics, while at the same time attenuating anti-analgesic effects, physical dependence, tolerance, hyperexcitability, hyperalgesia, and other undesirable (excitatory) side-effects typically caused by chronic use of bimodally-acting opioid agonists. As used herein, the term "opioid" refers to compounds which bind to specific opioid receptors and have agonist (activation) or antagonist (inactivation) effects at these receptors, such as opioid alkaloids, including the agonist morphine and the antagonist naloxone, and opioid peptides, including enkephalins and dynorphins. As used herein, the term "opiate" refers to drugs derived from opium or related analogs.

In the instant invention, a selective excitatory opioid receptor antagonist is combined with a reduced dose of a bimodally-acting opioid agonist so as to elicit the desired degree of analgesia (inhibitory effects) and attenuate undesired side-effects (excitatory effects). Opioid analgesia results from activation (by opioid agonists) of inhibitory opioid receptors on neurons in the nociceptive (pain) pathways of the peripheral and central nervous systems. The undesirable side-effects, including anti-analgesic actions, the development of physical dependence, some types of tolerance, hyperexcitability and hyperalgesia, result from sustained activation (by bimodally-acting opioid agonists) of excitatory opioid receptors on neurons in the nociceptive (pain) pathways of the peripheral and central nervous systems. The administration of selective excitatory receptor antagonists together with bimodally-acting opioid agonists enhances analgesic effects caused by said opioids and attenuates the development of physical dependence, tolerance and other undesirable side-effects which are also caused by said opioids. In addition, combined use of the opioid receptor antagonists and agonists of the invention can be used for more effective detoxification and treatment of opiate addicts.

BACKGROUND OF THE INVENTION

Morphine or other bimodally-acting opioid agonists are administered to relieve severe pain due to the fact that they have analgesic effects mediated by their activation of inhibitory opioid receptors on nociceptive neurons (see North, *Trends Neurosci.*, Vol. 9, pp. 114–117 (1986) and Crain and Shen, *Trends Pharmacol. Sci.*, Vol. 11, pp. 77–81 (1990)). However, bimodally-acting opioid agonists also activate opioid excitatory receptors on nociceptive neurons, which attenuates the analgesic potency of said opioids and results in the development of physical dependence thereon and increased tolerance thereto (see Shen and Crain, *Brain Res.*, Vol. 597, pp. 74–83 (1992)), as well as hyperexcitability, hyperalgesia and other undesirable (excitatory) side-effects. As a result, a long-standing need has existed to develop a method of both enhancing the analgesic (inhibitory) effects of bimodally-acting opioid agonists and limiting the undesirable (excitatory) side-effects caused by such opioid agonists.

The parent Patent Application for the instant invention, Ser. No. 07/947,690, relates to a specific group of opioid agonists for use as low/non-addictive analgesics and for the treatment of opioid addiction. In the parent Application, it is stated that this group of opioid agonists (which includes etorphine and dihydroetorphine) bind to and activate inhibitory but not excitatory opioid receptors. (In contrast, morphine and most other opioid alkaloids and peptides elicit bimodal effects by binding to and activating both excitatory and inhibitory opioid receptors.)

To date, no method has been discovered or developed whereby two opioid compounds are administered, one of which binds to and activates inhibitory opioid receptors to cause analgesia and the other of which binds to and inactivates excitatory opioid receptors so as to attenuate undesirable side-effects caused by the administration of bimodally-acting opioid agonists while simultaneously enhancing the analgesic effects of said bimodally-acting opioid agonists.

It is therefore an object of this invention to provide a method of enhancing the analgesic potency of morphine and other bimodally-acting opioid agonists by blocking their anti-analgesic side-effects.

It is a further object of this invention to provide a method of attenuating physical dependence, tolerance, hyperexcitability, hyperalgesia and other undesirable side-effects caused by the chronic administration of bimodally-acting opioid agonists.

It is another object of this invention to provide a method for detoxifying and treating opiate addicts utilizing excitatory opioid receptor antagonists.

It is yet another object of this invention to provide a composition which enhances the analgesic effects of bimodally-acting opioid agonists while simultaneously attenuating undesirable side-effects caused by said opioid agonists, including physical dependence, tolerance, hyperexcitability and hyperalgesia.

It is still a further object of this invention to provide a composition which is useful for detoxification and treatment of opiate addicts.

SUMMARY OF THE INVENTION

This invention is directed to a method of selectively enhancing the potency of morphine and other conventional bimodally-acting opioid agonists and simultaneously attenuating undesirable side-effects, including physical dependence, caused by the chronic administration of said opioid agonists. Morphine and other bimodally-acting (inhibitory/excitatory) opioid agonists bind to and activate inhibitory and excitatory opioid receptors on nociceptive neurons mediating pain. Activation of inhibitory receptors by said agonists causes analgesia. Activation of excitatory receptors by said agonists results in anti-analgesic effects, development of physical dependence, tolerance, hyperexcitability, hyperalgesia and other undesirable side-effects. The co-administration of an opioid antagonist which binds to and inactivates excitatory opioid receptors results in the blocking of excitatory anti-analgesic side-effects of said opioid agonists on these neurons, thereby resulting in enhanced analgesic potency which permits the use of lower doses of morphine or other conventional opioid analgesics.

The excitatory opioid receptor antagonists of the invention include etorphine, dihydroetorphine, diprenorphine and similarly acting opioid alkaloids and opioid peptides. The opioid agonists of the invention include morphine or other bimodally-acting (inhibitory/excitatory) opioid alkaloids or opioid peptides that are in clinical use as analgesics, including codeine, fentanyl analogs and endorphins.

In addition, combinations of an excitatory opioid receptor antagonist and morphine or another conventional bimodally-acting opioid analgesic can be used to detoxify and treat opiate addicts.

DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

Figure 1C:
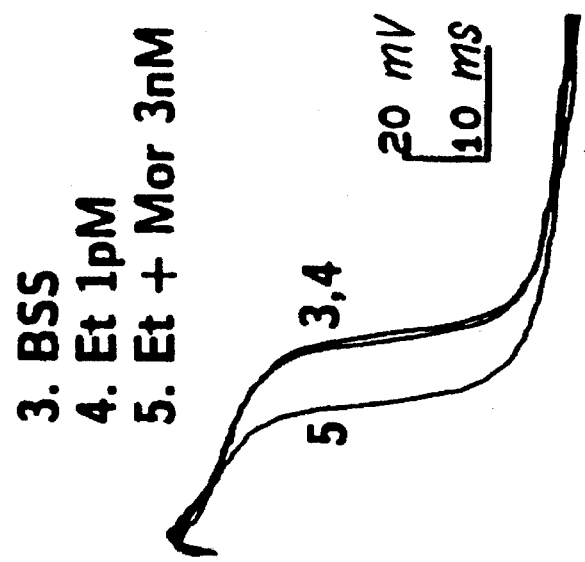
FIG. 1 represents the direct inhibitory effect of etorphine on the action potential duration (APD) of sensory neurons and the blocking effect of etorphine on the excitatory response (APD prolongation) elicited by morphine. Acute application of low (pM-nM) concentrations of etorphine to naive dorsal root ganglion (DRG) neurons elicits dose-dependent, naloxone-reversible inhibitory shortening of the APD. In contrast, morphine and other bimodally-acting opioid agonists elicit excitatory APD prolongation at these low concentrations which can be selectively blocked by <pM levels of etorphine.

This invention is directed to a method of selectively enhancing the analgesic effect caused by the administration of a bimodally-acting opioid agonist and simultaneously attenuating undesirable side-effects caused by the chronic administration of said bimodally-acting opioid agonists. This is performed by simultaneously inactivating excitatory opioid receptor-mediated functions of neurons in the nociceptive (pain) pathways and activating inhibitory opioid receptor-mediated functions of nociceptive neurons. A bimodally-acting opioid agonist and an excitatory opioid receptor antagonist are co-administered. The bimodally-acting opioid agonist binds to inhibitory receptors on nociceptive neurons so as to activate inhibitory opioid receptor-mediated functions, including analgesia, and concomitantly activates excitatory opioid receptors on nociceptive neurons. The excitatory opioid receptor antagonist binds to excitatory receptors on said neurons and thereby inactivates excitatory opioid receptor-mediated functions, including anti-analgesic effects, physical dependence and tolerance to the opioid agonist, hyperexcitability and hyperalgesia. In addition, this invention is directed to the use of said excitatory opioid receptor antagonists and opioid agonists to detoxify and treat opiate addicts. Further, this invention is directed to a composition comprising an excitatory opioid receptor antagonist and a bimodally-acting opioid agonist.

The inventors have discovered that certain compounds act as excitatory opioid receptor antagonists, that is, they bind to and inactivate excitatory opioid receptors on neurons in the pain pathways. The excitatory opioid receptor antagonists of the invention are preferably selected from the group consisting of etorphine, dihydroetorphine and diprenorphine. The opioid receptor antagonists of the invention inactivate mu, delta, kappa and other subtypes of excitatory opioid receptors. They may have varying structures. For example, etorphine and dihydroetorphine have very similar chemical structures and are considered to be potent analgesics which selectively activate inhibitory but not excitatory opioid receptors (see Shen and Crain, *Regulatory Peptides*, in press (1993)). In contrast, diprenorphine has a somewhat different chemical structure than etorphine and dihydroetorphine and has been previously considered to act as a universal opioid receptor antagonist by inactivating all types of inhibitory and excitatory opioid receptors (see Shen and Crain, *Brain Res.*, Vol. 491, pp. 227–242 (1989)). Nevertheless, these three compounds are all capable of selectively binding to and inactivating excitatory opioid receptors on nociceptive neurons when administered at low concentrations.

The bimodally-acting opioid agonists of this invention preferably include morphine, codeine, fentanyl analogs, endorphins, and other opioid alkaloids and opioid peptides. Typically, the opioid agonists of the invention are mu, delta, kappa or epsilon opioid receptor agonists, and are capable of binding to inhibitory opioid receptors on neurons in the pain pathway. When these bimodally-acting agonists bind to inhibitory opioid receptors, they thereby activate inhibitory opioid receptor-mediated functions, including analgesia.

As discussed below, the inventors have discovered that certain compounds (the excitatory opioid receptor antagonists of the invention), when co-administered with bimodally-acting opioid agonists, are capable at very low dosages of enhancing the analgesic effects of the bimodally-acting opioid agonists at least 10–1000 fold by inactivating excitatory anti-analgesic side-effects of said agonists. In addition, the excitatory opioid receptor antagonists of the invention inactivate other excitatory receptor-mediated functions, and thereby reduce the undesirable side-effects caused by said opioid agonists, including development of physical dependence, tolerance to the opioid agonists, hyperexcitability and hyperalgesia. In addition, the excitatory opioid receptor antagonists of the invention may be administered to detoxify and treat opiate addicts.

Ordinarily, bimodally-acting opioid agonists are administered clinically in pill form and are administered in milligram dosages. By co-administering bimodally-acting opioid agonists with the excitatory opioid receptor antagonists of the invention, it is possible to achieve an analgesic effect with 10–1000 times lower doses of the bimodally-acting opioid agonist than when said opioid agonist is administered alone. This is because the excitatory opioid receptor antagonists of the invention enhance the analgesic effects of the bimodally-acting opioid agonists by attenuating the anti-analgesic excitatory side-effects of said opioid agonists. Hence, bimodally-acting opioid agonists which are administered with the excitatory opioid receptor antagonists of the invention are administered in an amount 10–1000 times less than the amount of that bimodally-acting opioid agonist which has typically been administered for analgesia.

According to the present invention, the dose of excitatory opioid receptor antagonist to be administered is 10–1000 times less than the dose of bimodally-acting opioid agonist to be administered, for example, <1 microgram of said antagonist together with 10–100 micrograms of said agonist. These estimates of dosages are based on studies of neurons in culture. The excitatory opioid receptor antagonists, as well as the opioid agonists, can be administered sublingually, intramuscularly, subcutaneously or intraveneously.

The co-administration of the opioid agonists and excitatory opioid receptor antagonists of the invention simultaneously activates inhibitory functions of nociceptive neurons in the pain pathway and inactivates excitatory functions of the same or other nociceptive neurons. In order to demonstrate this, electrophysiologic studies on the effects of opioids on mouse sensory dorsal root ganglion neurons in tissue cultures were performed. It is shown below that this bimodal modulation is mediated by activating putative excitatory opioid receptors in addition to previously characterized inhibitory opioid receptors on sensory neurons.

It is shown that at low pM-nM concentrations, nearly all opioids, including morphine, enkephalins, dynorphins, endorphins and specific mu, delta and kappa opioid agonists, elicit naloxone-reversible dose-dependent excitatory effects manifested by prolongation of the calcium-dependent component of the action potential duration (APD) of dorsal root ganglia (DRG) neurons. In contrast, the same opioids generally elicit inhibitory APD shortening effects when applied at higher concentrations (0.1–1 µM).

The excitatory opioid effects on sensory neurons have been shown to be mediated by opioid receptors that are coupled via a cholera-toxin-sensitive stimulatory GTP-binding protein, Gs, to adenylate cyclase/cyclic AMP/protein kinase A-dependent ionic conductances that prolong the APD (resembling, for example, beta-adrenergic receptors). (See Crain and Shen, *Trends Pharmacol. Sci.*, Vol. 11, pp. 77–81 (1990)). On the other hand, inhibitory opioid effects are mediated by opioid receptors that are coupled via pertussis toxin-sensitive inhibitory G proteins: Gi to the adenylate cyclase/cyclic AMP system and Go to ionic conductances that shorten the APD (resembling, for example, $alpha_2$-adrenergic receptors). Shortening by opioids of the action potential of primary sensory neurons has generally been considered to be a useful model of their inhibition of calcium influx and transmitter release at presynaptic terminals in the dorsal spinal cord, thereby accounting for opioid-induced analgesia in vivo. (See North, *Trends Neurosci.*, Vol. 9, pp. 114–117 (1986) and Crain and Shen, *Trends Pharmacol. Sci.*, Vol. 11, pp. 77–81 (1990)). Similarly, the delayed repolarization associated with the observed opioid-induced prolongation of action potential has been interpreted as evidence of excitatory effects of opioids on sensory neurons that may result in enhanced calcium influx and transmitter release at presynaptic terminals. This could account for some types of hyperalgesia and hyperexcitatory states elicited by opioids in vivo (see Crain and Shen, *Trends Pharmacol. Sci.*, Vol. 11, pp. 77–81 (1990) and Shen and Crain, *Brain Res.*, Vol. 491, pp. 227–242 (1989).

Chronic treatment of DRG neurons with typical bimodally-acting (excitatory/inhibitory) opioids (e.g., 1 µM $D\text{-ala}^2\text{-D-leu}^5$ enkephalin (DADLE) or morphine for 1 week) results in tolerance to the usual inhibitory APD-shortening effects of high concentrations of these opioids and supersensitivity to the excitatory APD-prolonging effects of these opioid agonists, as well as the opioid antagonist, naloxone (see Crain and Shen, *Brain Res.*, Vol. 575, pp. 13–24 (1992) and Shen and Crain, *Brain Res.*, Vol. 597, pp. 74–83 (1992)). It has been suggested that the latter electrophysiologic effects and related biochemical adaptations are cellular manifestations of physical dependence that may underlie some aspects of opiate addiction (see Shen and Crain, *Brain Res.*, Vol. 597, pp. 74–83 (1992) and Terwilliger et al., *Brain Res.*, Vol. 548, pp. 100–110 (1991)).

In contrast to bimodally-acting opioids, it has been discovered by the inventors that the opioid alkaloids, etorphine (see Bentley and Hardy, *Proc. Chem. Soc.*, pp. 220 (1963)) and dihydroetorphine (see Bentley and Hardy, *J. Amer. Chem. Soc.*, Vol. 89, pp. 3281–3286 (1967)) uniquely elicit dose-dependent, naloxone-reversible inhibitory effects on sensory neurons in DRG-spinal cord explants, even at concentrations as low as 1 pM, and show no excitatory effects at lower concentrations (see Shen and Crain, *Regulatory Peptides*, in press (1993)). In addition, these potent inhibitory opioid receptor agonists also display unexpected antagonist effects at excitatory opioid receptors on DRG neurons. Acute pretreatment of DRG neurons with etorphine or dihydroetorphine, at low concentrations (<pM) which do not alter the APD, block the excitatory APD-prolonging effects of morphine and other bimodally-acting opioids and unmask inhibitory APD-shortening effects which normally require much higher concentrations. The potent inhibitory effect of etorphine and dihydroetorphine may be due to their selective activation of inhibitory opioid receptor-mediated functions while simultaneously inactivating excitatory opioid receptor-mediated functions in sensory neurons. In contrast, bimodally-acting opioids activate high-affinity excitatory as well as inhibitory opioid receptors on DRG neurons, thereby decreasing the net inhibitory effectiveness of these agonists, resembling the attenuation of the inhibitory potency of systemic morphine by the "anti-analgesic" (excitatory) effect of dynorphin A release in spinal cord in mice (see Fujimoto et al., *Neuropharmacol.*, Vol. 29, pp. 609–617, (1990)).

Acute application of pM-nM etorphine or dihydroetorphine to chronic μM morphine-treated DRG neurons elicited marked APD shortening (as in naive cells) even when added during naloxone-precipitated APD-prolongation in these sensitized cells, whereas 10 μM morphine or DADLE were ineffective and in contrast elicited a marked APD prolongation. These potent inhibitory effects of etorphine and dihydroetorphine on the action potential of chronic morphine-treated sensory neurons show remarkable mimicry of the rapid DHE-induced blockade of naloxone-evoked withdrawal syndromes in opiate-addicted animals and humans (see Wang et al., *Chinese J. Pharmacol. Toxicol.*, Vol. 6, pp. 36–40 (1992) and Qin, *Chinese J. Pharmacol. Toxicol.*, Vol. 6 (1992)) and the absence of cross-tolerance to etorphine in chronic morphine-treated mice even when the analgesic ED50 for morphine had increased 15-fold (see Lange et al., *Toxicol. Applied Pharmacol.*, Vol. 54, pp. 177–186 (1980)). Furthermore, chronic treatment of DRG neurons with 10 nM etorphine for >1 week did not result in opioid excitatory supersensitivity, i.e., APD prolongation following acute application of fM dynorphin A (1–13) or nM naloxone, nor tolerance to opioid inhibitory effects, all of which occur after chronic treatment with bimodally-acting opioids, e.g., DADLE or morphine (see Crain and Shen, *Brain Res.*, Vol. 575, pp. 13–24 (1992) and Shen and Crain, *Brain Res.*, Vol. 597, pp. 74–83 (1992)).

In vitro studies on sensory neurons suggested that an opioid which can selectively activate inhibitory, and inactivate excitatory, opioid receptor functions would be a unique analgesic in vivo with high potency, low dependence liability, and useful for treatment of opiate addicts.

EXAMPLE 1

Etorphine And Dihydroetorphine Act As Potent Selective Antagonists At Excitatory Opioid Receptors On DRG Neurons Thereby Enhancing Inhibitory Effects Of Bimodally-Acting Opioid Agonists Methods: The experiments described herein were carried out on dorsal root ganglion (DRG) neurons in organotypic explants of spinal cord with attached DRGs from 13-day-old fetal mice after 3 to 5 weeks of maturation in culture. The DRG-cord explants were grown on collagen-coated coverslips in Maximow depression-slide chambers. The culture medium consisted of 65% Eagle's minimal essential medium, 25% fetal bovine serum, 10% chick embryo extract, 2 mM glutamine and 0.6% glucose. During the first week in vitro the medium was supplemented with nerve growth factor (NGF-7S) at a concentration of about 0.5 μg/ml, to enhance survival and growth of the fetal mouse DRG neurons.

In order to perform electrophysiologic procedures, the culture coverslip was transferred to a recording chamber containing about 1 ml of Hanks' balanced salt solution (BSS). The bath solution was supplemented with 4 mM $Ca^{2+}$ and 5 mM $Ba^{2+}$ (i.e., Ca,Ba/BSS) to provide a prominent baseline response for pharmacological tests. Intracellular recordings were obtained from DRG perikarya selected at random within the ganglion. The micropipettes were filled with 3M KCl (having a resistance of about 60–100 megohms) and were connected via a chloridized silver wire to a neutralized input capacity preamplifier (Axoclamp 2A) for current-clamp recording. After impalement of a DRG neuron, brief (2 msec) depolarizing current pulses were applied via the recording electrode to evoke action potentials at a frequency of 0.1 Hz. Recordings of the action potentials were stored on a floppy disc using the P-clamp program (Axon Instruments) in a microcomputer (IBM AT-compatible).

Drugs were applied by bath perfusion with a manually operated, push-pull syringe system at a rate of 2–3 ml/min. Perfusion of test agents was begun after the action potential and the resting potential of the neuron reached a stable condition during >4 minute pretest periods in control Ca, Ba/BSS. Opioid-mediated changes in the APD were considered significant if the APD alteration was >10% of the control value for the same cell and was maintained for the entire test period of 5 minutes. The APD was measured as the time between the peak of the APD and the inflection point on the repolarizing phase. The following drugs were used: etorphine, diprenorphine and morphine (gifts from Dr. Eric Simon); dihydroetorphine (gift from Dr. B.-Y. Qin, China); naloxone (Endo Labs); DADLE, dynorphin and other opioid peptides (Sigma).

Opioid alkaloids and peptides were generally prepared as 1 mM solutions in $H_2O$ and then carefully diluted with BSS to the desired concentrations, systematically discarding pipette tips after each successive 1–10 or 1–100 dilution step to ensure accuracy of extremely low (fM-pM) concentrations.

Results: The opioid responsiveness of DRG neurons was analyzed by measuring the opioid-induced alterations in the APD of DRG perikarya. A total of 64 DRG neurons (from 23 DRG-cord explants) were studied for sensitivity to progressive increases in the concentration of etorphine (n=30) or dihydroetorphine (n=38). Etorphine rapidly and dose-dependently shortened the APD in progressively larger fractions of DRG cells at concentrations from 1 fM (30% of cells; n=26) to 1 μM (80% of cells; n=16) (see FIGS. 1 and 2).

Figure 1C:
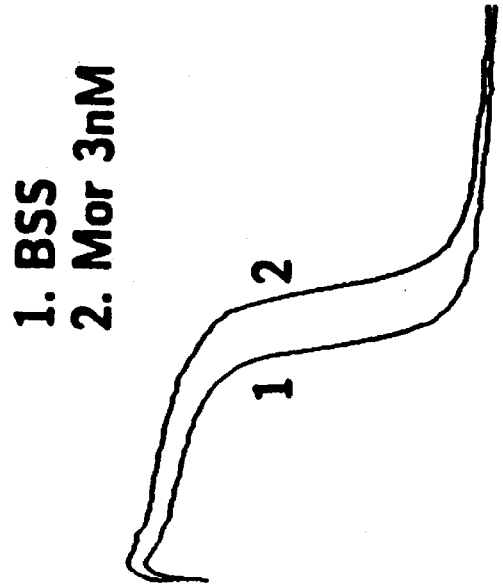

FIG. 1 shows that acute application of low (pM-nM) concentrations of etorphine to naive DRG neurons elicits dose-dependent, naloxone-reversible inhibitory shortening of the action potential duration (APD). In contrast, dynorphin (and many other bimodally-acting opioid agonists, e.g., morphine, DADLE) elicit excitatory APD prolongation at these low concentrations (see FIG. 2), which can be selectively blocked by <pM levels of etorphine or diprenorphine (see FIG. 3). FIG. 1A record 1 shows the action potential (AP) generated by a DRG neuron in balanced salt solution containing 5 mM $Ca^{2+}$ and 5 mM $Ba^{2+}$ (BSS). AP response in this record (and in all records below) is evoked by a brief (2 msec) intracellular depolarizing current pulse. FIG. 1A records 2–5 show that APD is not altered by bath perfusion with 1 fM etorphine (Et) but is progressively shortened in 1 pM, 1 nM and 1 μM concentrations (5 minute test periods). FIG. 1A record 6 shows that APD returns to control value after transfer to BSS (9 minute test). FIG. 1B records 1 and 2 show that APD of another DRG neuron is shortened by application of 1 nM etorphine (2 minute test). FIG. 1B record 3 shows that APD returns to control value after transfer to 10 nM naloxone (NLX). FIG. 1B records 4 and 5 show that APD is no longer shortened by 1 nM or even 1 μM etorphine when co-perfused with 10 nM naloxone (5 minute test periods). FIG. 1C records 1 and 2 show that APD of another DRG neuron is prolonged by application of 3 nM morphine. FIG. 1C record 3 shows that APD returns to control value by 5 minutes after washout. FIG. 1C record 4 shows that application of 1 pM etorphine does not alter the APD. FIG. 1C record 5 shows that APD is no longer prolonged by 3 nM morphine when co-perfused with 1 pM etorphine and instead is markedly shortened to a degree which would require a much higher morphine concentration in the absence of etorphine. Similar results were obtained by pretreatment with 1 pM diprenorphine (see FIG. 3). Records in this and subsequent Figures are from DRG neurons in organotypic DRG-spinal cord explants maintained for 3–4 weeks in culture.

Figure 2:
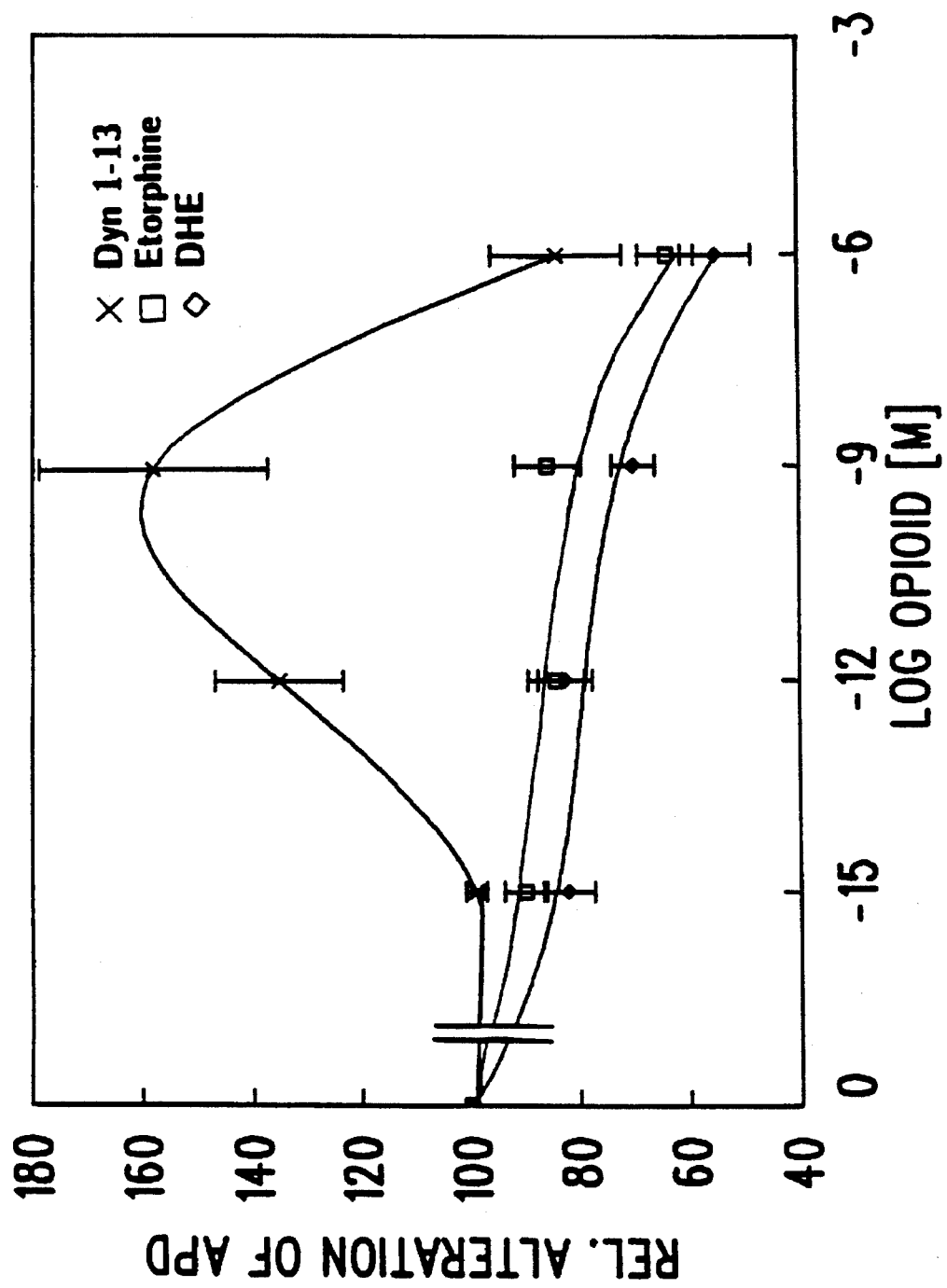
FIG. 2 represents dose-response curves of different opioids, showing that etorphine and dihydroetorphine elicit only inhibitory dose-dependent shortening of the APD of DRG neurons at all concentrations tested (fM-µM). In contrast, dynorphin A (as well as morphine and other bimodally-acting opioids) elicits dose-dependent excitatory APD prolongation at low concentrations (fM-nM) and requires much higher concentrations (about 0.1–1 µM) to shorten the APD, thereby resulting in a bell-shaped dose-response curve.

FIG. 2 shows dose-response curves demonstrating that etorphine (Et) (□) and dihydroetorphine (DHE) (◊) elicit only inhibitory dose-dependent shortening of the APD of DRG neurons at all concentrations tested (fM-μM). In contrast, dynorphin A (1–13) (Dyn) (X) (as well as morphine and other bimodally-acting opioids) elicits dose-dependent excitatory APD prolongation at low concentrations (fM-nM) and generally requires much higher concentrations (about 0.1–1 μM) to shorten the APD, thereby resulting in a bell-shaped dose-response curve. Data were obtained from 11 neurons for the etorphine tests, 13 for the DHE tests and 35 for the dynorphin tests; 5, 8 and 9 neurons were tested (as in FIG. 1) with all four concentrations of etorphine, DHE and dynorphin, respectively (from fM to μM). For sequential dose-response data on the same neuron, the lowest concentrations (e.g., 1 fM) were applied first.

Dihydroetorphine was even more effective (n=38; FIG. 2). Naloxone (10 nM) prevented the etorphine- and dihydroetorphine-induced APD shortening which was previously elicited in the same cells (n=12; FIG. 1B). These potent inhibitory effects of etorphine and dihydroetorphine on DRG neurons at low concentrations are in sharp contrast to the excitatory APD-prolonging effects observed in similar tests with morphine and a wide variety of mu, delta and kappa opioids. None of the DRG neurons tested with different concentrations of etorphine or dihydroetorphine showed prominent APD prolongation.

The absence of excitatory APD-prolonging effects of etorphine and dihydroetorphine on DRG neurons could be due to low binding affinity of these opioid agonists to excitatory opioid receptors. Alternatively, these opioids might bind strongly to excitatory receptors, but fail to activate them, thereby functioning as antagonists. In order to distinguish between these two modes of action, DRG neurons were pretreated with etorphine at low concentrations (fM-pM) that evoked little or no alteration of the APD. Subsequent addition of nM concentrations of morphine, DAGO, DADLE or dynorphin to etorphine-treated cells no longer evoked the usual APD prolongation observed in the same cells prior to exposure to etorphine (n=11; see FIG. 1C). This etorphine-induced blockade of opioid excitatory effects on DRG neurons was often effective for periods up to 0.5–2 hours after washout (n=4).

These results demonstrate that etorphine, which has been considered to be a "universal" agonist at mu, delta and kappa opioid receptors (see Magnan et al., *Naunyn-Schmiedleberg's Arch. Pharmacol.*, Vol. 319, pp. 197–205 (1982)), has potent antagonist actions at mu, delta and kappa excitatory opioid receptors on DRG neurons, in addition to its well-known agonist effects at inhibitory opioid receptors. Pretreatment with dihydroetorphine (fM-pM) showed similar antagonist action at excitatory opioid receptor mediating nM opioid-induced APD prolongation (n=2). Furthermore, after selective blockade of opioid excitatory APD-prolonging effects by pretreating DRG neurons with low concentrations of etorphine (fM-pM), which showed little or no alteration of the APD, fM-nM levels of bimodally-acting opioids now showed potent inhibitory APD-shortening effects (5 out of 9 cells) (see FIG. 1C and FIG. 3). This is presumably due to unmasking of inhibitory opioid receptor-mediated functions in these cells after selective blockade of their excitatory opioid receptor functions by etorphine.

EXAMPLE 2

Diprenorphine At Low Concentration Also Shows Potent Selective Antagonist Action At Excitatory Opioid Receptors Drug tests: Mouse DRG-cord explants, grown for >3 weeks as described in Example 1, were tested with the opioid antagonist, diprenorphine. Electrophysiological recordings were made as in Example 1.

Results: The "universal" opioid receptor antagonist, diprenorphine was previously shown to block, at nM concentrations, both inhibitory APD shortening of DRG neurons by μM opioid agonists as well as excitatory APD prolongation by nM opioids. Tests at lower concentrations have revealed that pM diprenorphine acts selectively as an antagonist at mu, delta and kappa excitatory opioid receptors, comparable to the antagonist effects of pM etorphine and dihydroetorphine. In the presence of pM diprenorphine, morphine (n=7) and DAGO (n=7) no longer elicited APD prolongation at low (pM-nM) concentrations (see FIG. 3A). Instead, they showed progressive dose-dependent APD shortening throughout the entire range of concentrations from fM to μM (see FIG. 3B), comparable to the dose-response curves for etorphine and dihydroetorphine (see FIG. 2 and FIG. 1C). This unmasking of inhibitory opioid receptor-mediated APD-shortening effects by pM diprenorphine occurred even in the presence of $10^6$-fold higher concentrations of morphine (see FIG. 3A, records 11 vs. 5).

Figure 3A:
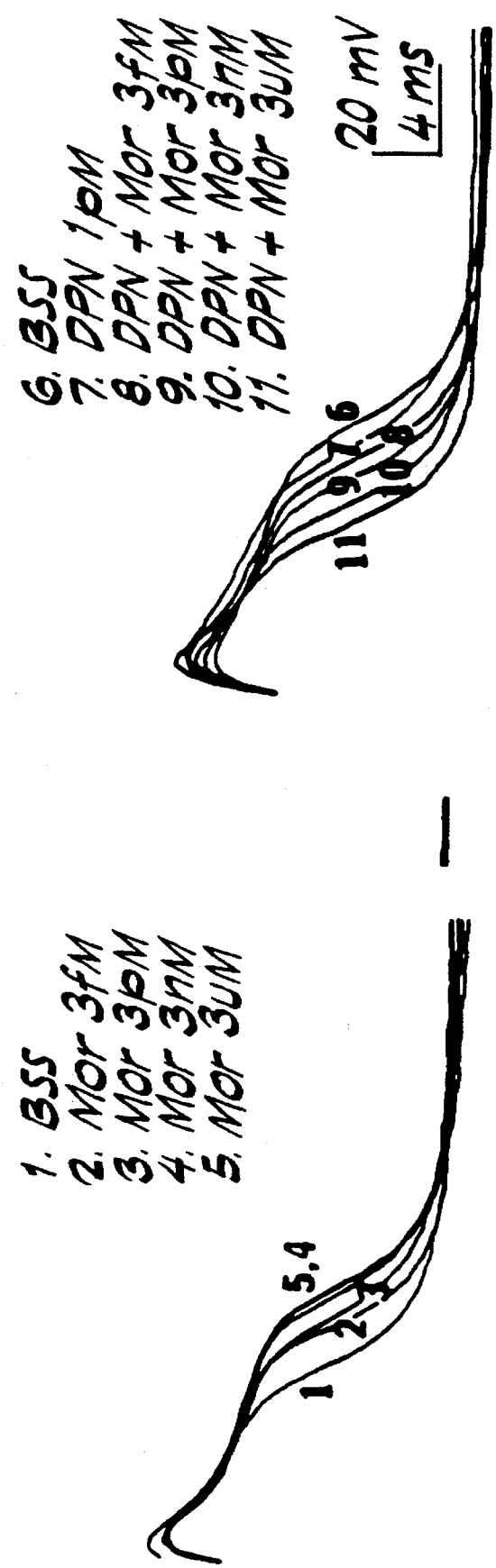
FIG. 3 is comprised of FIG. 3A and 3B, and represents the selective blocking of excitatory APD-prolonging effects elicited by morphine in DRG neurons by co-administration of a low (pM) concentration of diprenorphine, thereby unmasking potent dose-dependent inhibitory APD shortening by low concentrations of morphine.
Figure 3B:
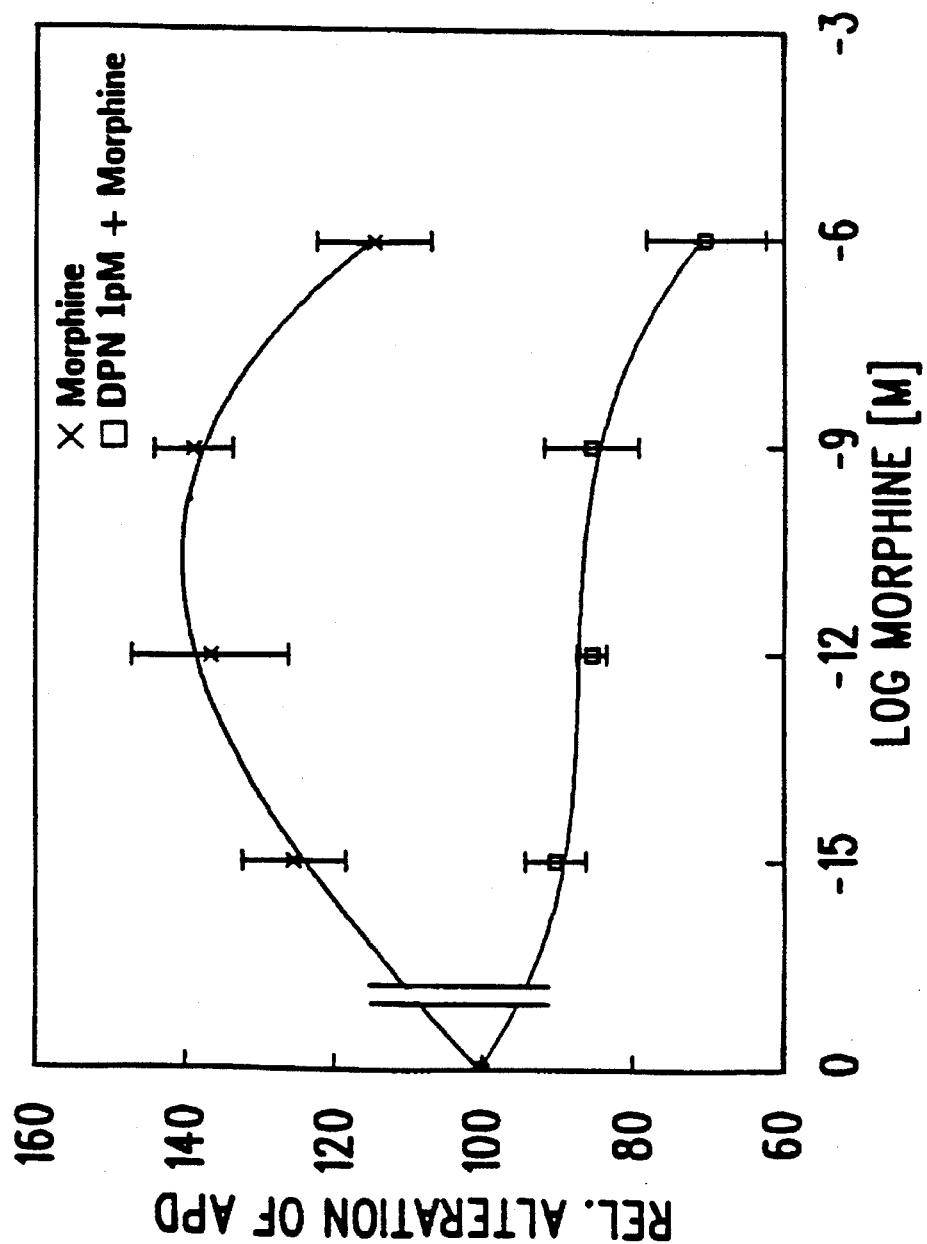

FIG. 3 shows that excitatory APD-prolonging effects elicited by morphine in DRG neurons are selectively blocked by co-administration of a low (pM) concentration of diprenorphine, thereby unmasking potent dose-dependent inhibitory APD shortening by low concentrations of morphine. FIG. 3A records 1–4 show that APD of a DRG neuron is progressively prolonged by sequential bath perfusions with 3 fM, 3 pM and 3 nM morphine (Mor). FIG. 3A record 5 shows that APD of this cell is only slightly shortened after increasing morphine concentration to 3 μM. FIG. 3A records 6 and 7 show that after transfer to BSS, the APD is slightly shortened during pretreatment for 17 minutes with 1 pM diprenorphine (DPN). FIG. 3A records 8–11 show that after the APD reached a stable value in DPN, sequential applications of 3 fM, 3 pM, 3 nM and 3 μM Mor progressively shorten the APD, in contrast to the marked APD prolongation evoked by these same concentrations of Mor in the absence of DPN (see also FIG. 1C). FIG. 3B dose-response curves demonstrate similar unmasking by 1 pM DPN of potent dose-dependent inhibitory APD shortening by morphine (X) in a group of DRG neurons (n=7), all of which showed only excitatory APD prolongation responses when tested prior to introduction of DPN (X). Note that the inhibitory potency of morphine in the presence of pM DPN becomes comparable to that of etorphine and diprenorphine (see FIG. 2).

EXAMPLE 3

Enhanced Inhibitory Effect of Etorphine and Dihydroetorphine On Chronic Opioid-Treated Sensory Neurons Which Become Supersensitive To Opioid Excitatory Effects Drug tests: Mouse DRG-cord explants, grown for >3 weeks as described in Example 1, were chronically exposed to the bimodally-acting (excitatory/inhibitory) delta/mu opioid agonist, DADLE (1 µM) or morphine (1 µM) for 1 week or longer and tested acutely with etorphine or dihydroetorphine. Electrophysiological recordings were made as in Example 1.

Results: Acute application of fM etorphine to chronic µM DADLE- or morphine-treated DRG neurons (for >1 week) was still effective in shortening the APD in 30% of the treated neurons (n=23) when tested in the presence of µM DADLE or morphine (see FIG. 4). Furthermore, pM levels of etorphine shortened the APD in 76% of the cells tested (n=21).

Figure 4:
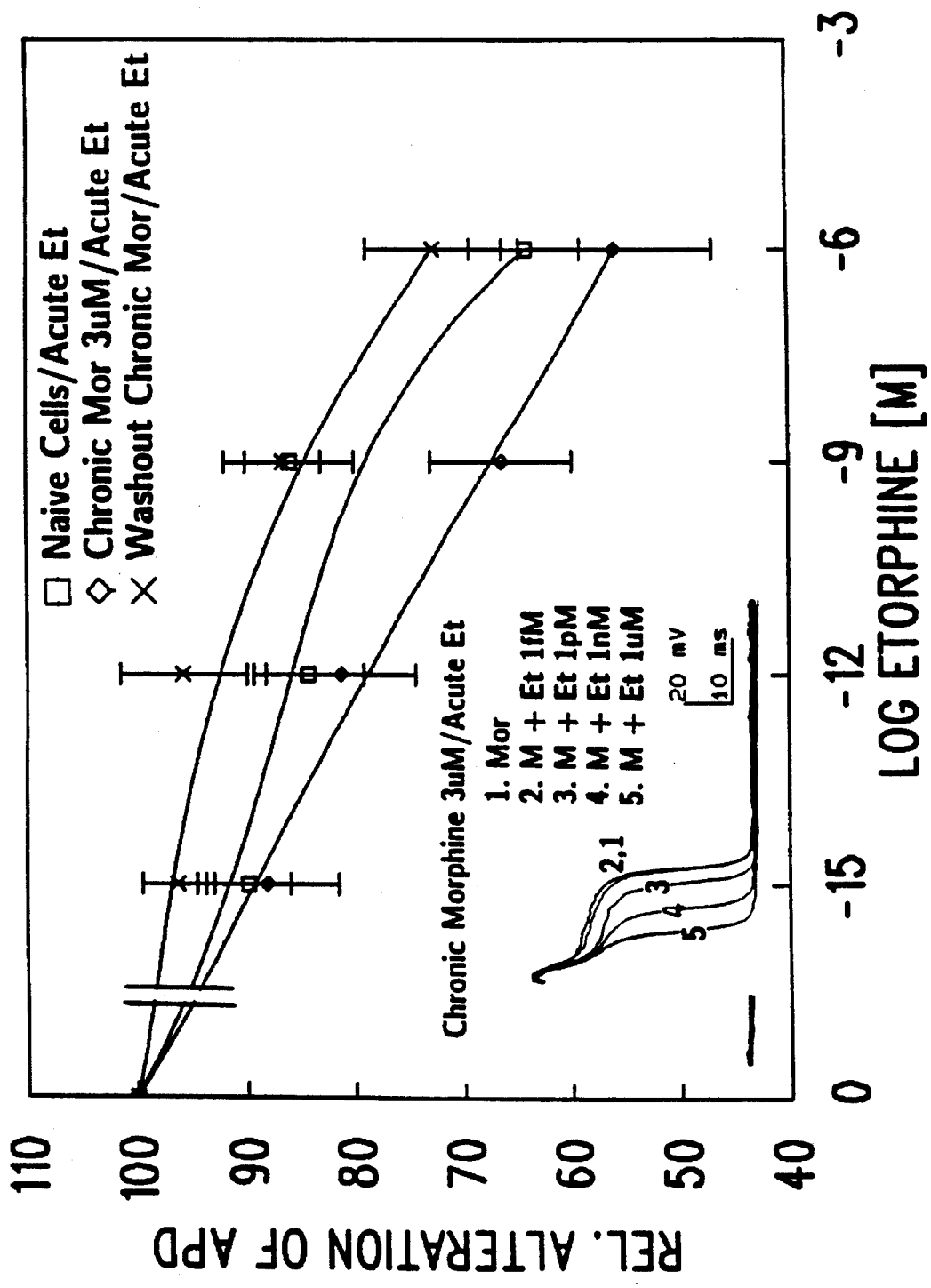
FIG. 4 represents the blocking of supersensitive excitatory APD-prolonging effect of DRG neurons after chronic morphine exposure by the excitatory opioid receptor antagonist, etorphine. After chronic exposure to morphine or other bimodally-acting opioids, DRG neurons become supersensitive to the excitatory APD prolonging effects of these opioids, whereas etorphine becomes even more effective in eliciting inhibitory shortening of the APD of the same DRG neurons when tested in the presence of the chronic opioid. The apparent enhancement in inhibitory potency of etorphine on chronic morphine-treated neurons is due to the unmasking of inhibitory APD shortening effects of morphine following etorphine-antagonist action at excitatory opioid receptors.

FIG. 4 shows that after chronic exposure to morphine (Mor), or other bimodally-acting opioids, DRG neurons become supersensitive to the excitatory APD-prolonging effects of these opioids, whereas etorphine (Et) becomes even more effective in eliciting inhibitory shortening of the APD of the same DRG neurons when tested acutely in the presence of the chronic opioid. Dose-response curves show that after chronic treatment of DRG neurons with 3 µM Mor for 2-3 weeks in culture, the magnitude of APD shortening elicited by acute application of Et ($\Diamond$) is markedly enhanced at all test concentrations (fM-µM); see typical records in Inset), thereby shifting the dose-response curve sharply to the left, as compared to data obtained from naive DRG neurons ($\square$). In contrast, after washout of the chronic morphine with BSS, retests of sequentially increasing concentrations of Et from fM to µM result in less prominent APD shortening (X), comparable to, or even weaker than, Et effects on naive cells ($\square$). These results suggest that the apparent enhancement in inhibitory potency of Et on chronic Mor-treated neurons is actually due to unmasking of inhibitory APD-shortening effects of chronic Mor following Et-antagonist action at excitatory opioid receptors, as occurs in tests on naive DRG cells (see FIG. 1C). As shown in the inset, FIG. 4 record 1 shows AP generated by a DRG neuron treated for 3 weeks in culture with 3 µM Mor and then tested in BSS in the presence of the chronic Mor. FIG. 4 record 2 shows that 1 fM Et does not alter the APD in the presence of 3 µM Mor. FIG. 4 records 3-5 show that sequential increases in the concentration of Et from 1 pM to 1 µM progressively shortens the APD in the presence of 3 µM Mor (whereas dynorphin dose-dependently prolonged the APD of the same chronic opioid-treated cell — not shown; see FIG. 2).

In contrast, morphine, DADLE and other chronic bimodally-acting opioid-treated DRG neurons showed supersensitive excitatory APD-prolonging effects when tested with low (fM-pM) concentrations of dynorphin (1–13) before (n=13) or after (n=6) washout of the chronic DADLE or morphine. The effectiveness of etorphine in eliciting inhibitory APD-shortening in chronic opioid-treated DRG neurons appeared to be significantly enhanced relative to naive cells.

Whereas nM etorphine moderately shortened the APD of naive DRG neurons (mean decrease to about 86+6%; n=18; see FIGS. 1A and 2), this low concentration was much more effective on chronic morphine-treated DRG neurons (mean decrease to 66%+7% (n=9)), when tested in the presence of morphine (FIG. 4). Dose-response tests of etorphine on chronic DADLE- or morphine-treated DRG neurons showed that the magnitude of the APD was progressively shortened when the acute etorphine concentration was tested sequentially from 1 fM to 1 µM in the presence of µM DADLE or morphine (FIG. 4). On the other hand, after washout of the chronic morphine, acute application of etorphine to chronic µM opioid-treated DRG neurons no longer showed greater inhibitory effectiveness as compared to tests on naive cells (n=10) (FIG. 4). These results suggest that the apparent enhancement in inhibitory effectiveness of etorphine (and dihydroetorphine), when tested during chronic exposure to bimodally-acting opioid-treated DRG neurons, is due to their dual synergistic action as agonists at inhibitory opioid receptors and antagonists at excitatory opioid receptors. The latter property results in unmasking of the inhibitory actions of the chronic DADLE or morphine, as occurs in similar tests on naive neurons (see FIG. 1C and FIG. 3). Acute application of dihydroetorphine to chronic µM morphine-treated DRG neurons indicated that this opioid showed even greater inhibitory potency than etorphine. fM concentrations shortened the APD in 80% of the treated cells (n=10) and pM (or higher) levels were effective on all cells tested in the presence of the chronic opioid (n=10).

Thus, etorphine and dihydroetorphine show similarly remarkable effectiveness as diprenorphine in antagonizing excitatory opioid receptors even when tested in the presence of $10^6$–$10^9$ higher concentrations of morphine or DADLE. As a result of these unusual properties, etorphine and dihydroetorphine showed no cross-tolerance in tests on chronic DADLE- or morphine-treated DRG neurons, just as chronic morphine-treated mice showed no cross-tolerance to etorphine even when the analgesic ED for morphine had increased 15-fold (see Lange et al., *Toxicol. Applied Pharmacol.*, Vol. 54, pp. 177–186 (1980)). The absence of cross-tolerance to etorphine in chronic morphine-treated DRG neurons is in sharp contrast to the attenuated inhibitory effects (i.e., tolerance) and the enhanced excitatory effects (i.e., "dependence") displayed by all bimodally-acting mu, delta and kappa opioid agonists when tested acutely on these chronic opioid-treated cells.

EXAMPLE 4

Etorphine Or Dihydroetorphine Can Block Naloxone-Precipitated Supersensitive Excitatory Effects In Chronic Opioid-Treated DRG Neurons Drug tests: Mouse DRG-cord explants, grown for >3 weeks as described in Example 1, were chronically exposed to the bimodally-acting (excitatory/inhibitory) delta/mu opioid agonist, DADLE (1 µM or morphine (1 µM) for 1 week or longer. The excitatory opioid supersensitivity of chronic opioid-treated DRG neurons was precipitated by naloxone (1 nM). Electrophysiological recordings were made as in Example 1.

Results: The opioid antagonist, naloxone (1 nM–1 µM) does not alter the APD of naive DRG neurons. In contrast, after chronic opioid treatment (as well as after acute GM1 ganglioside treatment) excitatory opioid receptor functions become so supersensitive that acute application of low concentrations of naloxone prolonged the APD of the treated sensory neurons, presumably due to weak partial agonist properties of naloxone at excitatory opioid receptors (see Crain and Shen, *Brain Res.*, Vol. 575, pp. 13–24 (1992) and Crain and Shen, *J. Pharmacol. Exp. Ther.*, Vol. 260, pp. 182–186 (1992)). Naloxone (1 nM) elicited excitatory APD-prolonging effects in 92% of the chronic μM DADLE- or morphine-treated DRG neurons tested in the present study (n=12) (see FIG. 5).

These results provide a novel cellular model to account for naloxone-precipitated withdrawal supersensitivity in opiate addicts in vivo. It should be emphasized that naloxone was not simply blocking the inhibitory effect of residual DADLE or morphine since the treated DRG neurons were already tolerant to these APD-shortening effects. It is therefore of great interest that acute application of remarkably low concentrations of etorphine (fM-nM) to chronic μM morphine or DADLE-treated cells could effectively block naloxone-induced APD prolongation in all of the treated DRG neurons (n=18) (see FIG. 5), thereby mimicking the potent effects of the related etorphine analog dihydroetorphine in suppressing naloxone-evoked withdrawal symptoms in opiate addicts (see Wang et al., *Chinese J. Pharmacol. Toxicol.*, Vol. 6, pp. 36–40 (1992)).

Figure 5:
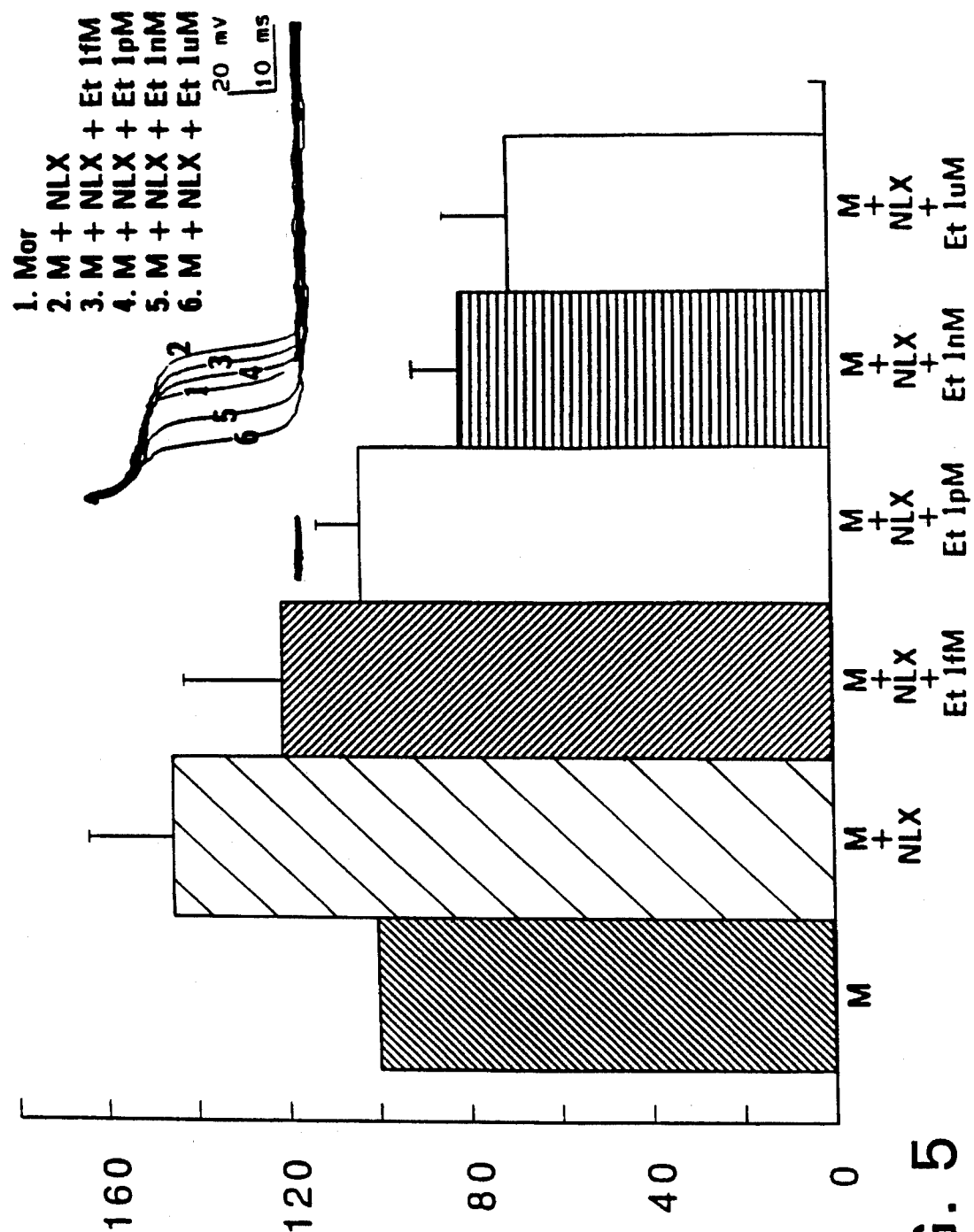
FIG. 5 represents the blocking effect of etorphine on naloxone-precipitated excitatory APD prolongation of DRG neurons after chronic exposure to morphine or other bimodally-acting opioids. Acute application of low concentrations of etorphine can dose-dependently block the excitatory APD-prolonging effects of naloxone on these supersensitive DRG neurons.

FIG. 5 shows that after chronic exposure to morphine (Mor) or other bimodally-acting opioids, acute application of low concentrations of etorphine (Et) can dose-dependently block the excitatory APD-prolonging effects of naloxone (NLX) on these supersensitive DRG neurons. Histogram shows that acute application of 1 nM NLX to DRG neurons chronically treated with 3 μM Mor for 1–4 weeks prolonged the APD by about 50%, tested in the presence of 3 μM Mor. See also Inset: records 1 and 2. In contrast, NLX (nM-μM) does not alter the APD of naive DRG neurons. Sequential co-perfusions with 1 fM to 1 μM Et elicit dose-dependent attenuation of the NLX-induced APD prolongation in these treated neurons, resulting in shortening of the APD to about 70% of the control value in 1 μM Et. In contrast, NLX-pretreatment of naive DRG neurons blocks Et-induced APD shortening (see FIG. 1B). Inset records 1 and 2 show that 1 nM NLX prolongs the APD of a DRG neuron after chronic 3 μM Mor treatment for 2 weeks and tested in the presence of 3 μM Mor (5 minute test). Inset record 3 shows that acute addition of 1 fM Et attenuates the NLX-induced APD prolongation (5 minute test). Inset record 4 shows that increasing the concentration of Et to 1 pM almost completely blocks the NLX-induced APD prolongation. Inset records 5 and 6 show that sequential application of 1 nM and 1 μM Et in the presence of Mor and NLX results in progressive shortening of the APD well below the initial magnitude in chronic Mor (as shown in FIG. 4).

These results suggest that the potent dose-dependent effects of etorphine and dihydroetorphine in blocking naloxone-evoked APD prolongation in chronic opioid-treated DRG neurons in vitro and withdrawal syndromes in opiate addicts in vivo is due to the strong antagonist actions of these opioids at supersensitive excitatory opioid receptors which have become responsive to the weak agonist properties of naloxone. This is in sharp contrast to the blockade of etorphine-induced APD shortening in naive DRG neurons by naloxone under conditions where it acts primarily as an antagonist at inhibitory opioid receptors (see FIG. 5 and FIG. 1B).

EXAMPLE 5

In The Presence Of Etorphine, Chronic Morphine Treatment Of DRG Neurons No Longer Results In Development Of Opioid Excitatory Supersensitivity And Tolerance Drug tests: Mouse DRG-cord explants, grown for >3 weeks as described in Example 1, were chronically exposed to bimodally-acting opioid agonist, morphine (1 μM) and opioid excitatory receptor antagonist, etorphine (1 pM) for >1 week and tested for opioid excitatory supersensitivity of DRG neurons at low concentrations of naloxone or dynorphin A (1–13) and tolerance to the opioid inhibitory effects of APD with high concentrations of morphine. Electrophysiological recordings were made as in Example 1.

Results: Co-administration of low (pM) concentrations of etorphine during chronic treatment of DRG neurons with μM levels of morphine was remarkably effective in preventing development of the opioid excitatory supersensitivity and tolerance that generally occurs after sustained exposure to bimodally-acting opioids. Acute application of 1 fM dynorphin (1–13) (n=10) or 10 nM naloxone (n=8) to DRG neurons chronically exposed to 3 μM morphine together with 1 pM etorphine (for >1 week) did not evoke the usual excitatory APD prolongation observed in chronic morphine-treated cells, even when tested up to 6 hours after return to BSS. Furthermore, there was little or no evidence of tolerance to the inhibitory effects of μM morphine: 6 out of 10 cells still showed APD shortening following acute application of μM morphine similar to tests on naive DRG cells. If etorphine was acting simply as an agonist at inhibitory opioid receptors, one might predict that the addition of 1 pM etorphine together with a $10^6$-fold higher concentration of morphine would have a negligible effect on chronic morphine-treated DRG neurons or would augment development of cellular signs of dependence. On the other hand, the results are readily accounted for by the potent antagonist action of etorphine at excitatory opioid receptors during chronic morphine treatment, thereby preventing development of opioid excitatory supersensitivity and tolerance, just as occurs during chronic opioid treatment of DRG neurons in the presence of cholera toxin-B subunit (see Shen and Crain, *Brain Res.*, Vol. 597, pp. 74–83 (1992)). This toxic subunit selectively interferes with GM1 ganglioside regulation of excitatory opioid receptor functions (see Shen and Crain, *Brain Res.*, Vol. 531, pp. 1–7 (1990) and Shen et al., *Brain Res.*, Vol. 559, pp. 130–138 (1991)).

EXAMPLE 6

Chronic Etorphine-Treated DRG Neurons Do Not Develop Opioid Excitatory Supersensitivity Or Tolerance Drug tests: Mouse DRG-cord explants, grown for >3 weeks as described in Example 1, were chronically exposed to etorphine (nM) for >1 week and tested for opioid excitatory supersensitivity of DRG neurons to low concentrations of naloxone or dynorphin A (1–13) and tolerance to the inhibitory effects of higher concentrations of etorphine.

Results: Chronic treatment of DRG neurons with etorphine alone even at a relatively high concentration (10 nM) for >1 week in culture also did not result in opioid excitatory supersensitivity when tested acutely with 1 fM dynorphin (1–13) (26 out of 28 cells) or 1–10 nM naloxone (13 out of 14 cells), either before or after withdrawal of the chronic etorphine (FIG. 6).

Figure 6:
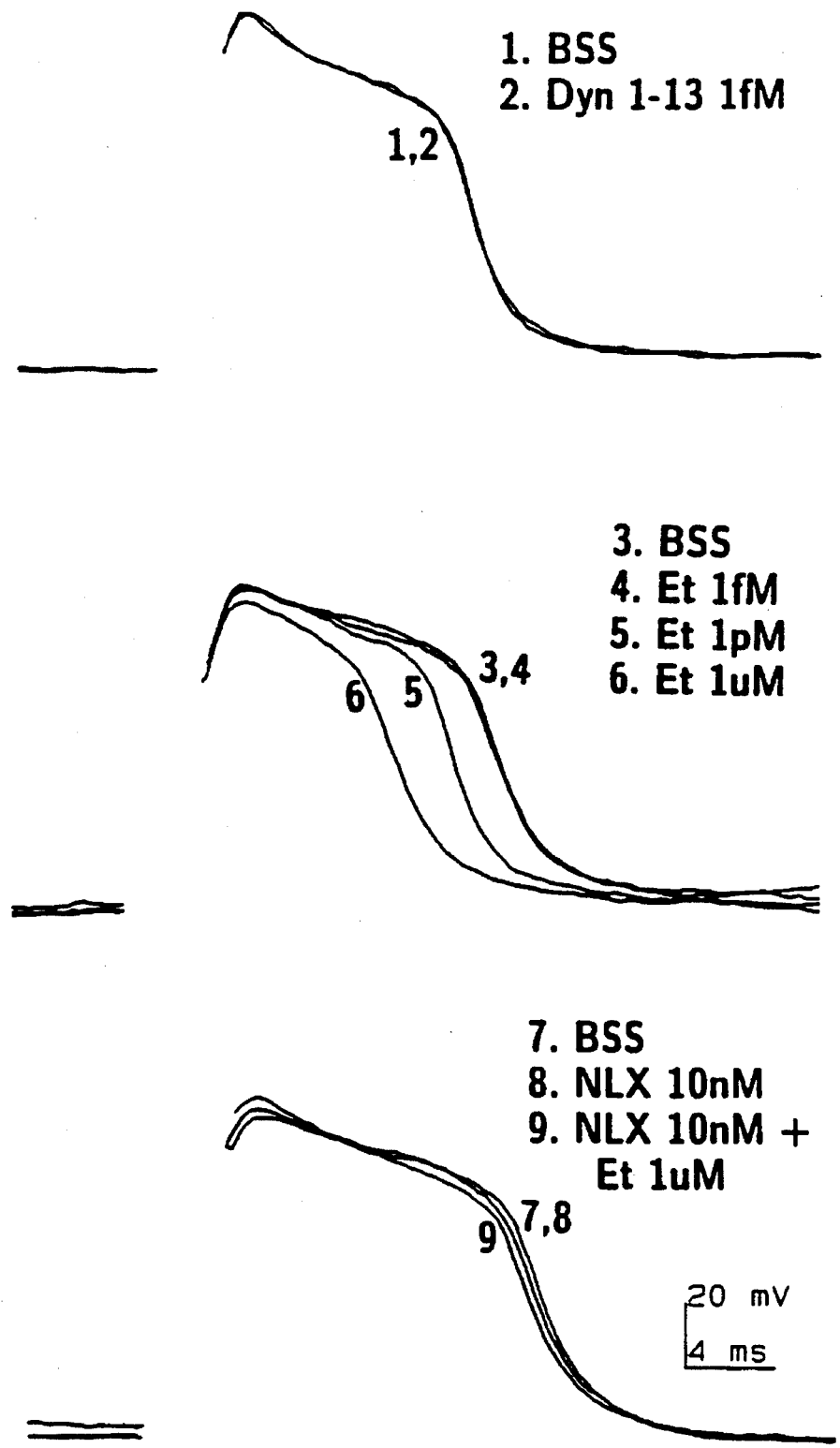
FIG. 6 represents the ability of etorphine to elicit sustained inhibitory effects without causing supersensitivity and tolerance in DRG neurons after chronic treatment. Chronic exposure of etorphine (nM) to DRG neurons did not elicit supersensitive excitatory responses (APD prolongation) to low test concentrations of dynorphin A (1–13) and naloxone nor did these cells develop tolerance to the inhibitory effects of etorphine or other opioid agonists.

FIG. 6 shows that after chronic exposure to nM etorphine (Et), DRG neurons do not become supersensitive to the excitatory effects of dynorphin 1–13 (Dyn) and naloxone (NLX), nor do they develop tolerance to the inhibitory effects of etorphine or other opioid agonists. Record 1 shows the action potential (AP) generated by a DRG neuron after chronic 10 nM Et treatment for 20 days and tested in balanced salt solution (BSS) shortly after washout of the Et. Record 2 shows that APD is not altered by 1 fM Dyn. Records 3–6 show that APD is not altered by bath perfusion with 1 fM Et but is progressively shortened by 1 pM and 1 µM concentrations (5 minute test periods). Records 7 and 8 show that APD of the same neuron is not altered by application of 10 nM NLX. Record 9 shows that APD is no longer shortened by 1 µM Et when co-perfused with 10 nM naloxone (5 minute test period).

After etorphine withdrawal for about 1 hour, 1 nM dynorphin (1–13) shortened the APD in 3 cells or did not show typical APD prolongation (10 out of 11 cells), resembling the attenuation of opioid excitatory effects and unmasking of opioid inhibition observed in acute tests on naive cells after washout of low (pM) concentrations of etorphine (see FIG. 1C). Furthermore, after washout of the chronic 10 nM etorphine, acute application of pM, nM and µM etorphine elicited similar APD shortening (in 3 out of 4 cells tested at each concentration) as observed in naive cells. Thus chronic 10 nM etorphine treatment of DRG neurons did not result in the characteristic cellular signs of physical dependence and tolerance that occurred after chronic exposure of these cells to morphine and other bimodally-acting opioids.

Estimates Of Specific In Vivo Dosages Of Excitatory Opioid Receptor Antagonists That May Enhance Analgesic Potency And Reduce Dependence Liability (And Other Side-Effects) Of Morphine Or Other Conventional Opioid Analgesics When Administered In Combination Electrophysiological studies on DRG neurons indicated that pre-treatment with low fM–pM concentrations of etorphine, dihydroetorphine and diprenorphine are remarkably effective in blocking excitatory APD-prolonging effects of morphine bimodally-acting opioid agonists by selective antagonist actions at mu, delta and kappa excitatory opioid receptors. The potency of these three excitatory opioid receptor antagonists is clearly shown by their ability to unmask inhibitory opioid receptor-mediated APD-shortening effects, even in presence of $10^6$-fold higher concentrations of morphine other bimodally-acting opioid agonists (FIGS. 3–5).

In the presence of these selective excitatory opioid receptor antagonists, morphine and other clinically used opioids showed markedly increased potency in evoking the inhibitory effects on the action potential of sensory neurons which are generally considered to underly opioid analgesic action in vivo. These bimodally-acting opioid agonists became effective in shortening, instead of prolonging, the APD at pM-nM (i.e., $10^{-12}$–$10^{-9}$M) concentrations, whereas 0.1–1 pM (i.e., $10^{-7}$–$10^{-6}$M) levels were generally required to shorten the APD (FIG. 2). Selective blockade of the excitatory side-effects of these bimodally-acting opioid agonists eliminates the attenuation of their inhibitory effectiveness that would otherwise occur. Hence, according to this invention, the combined use of a relatively low dose of one of these selective excitatory opioid receptor antagonists, together with morphine or other bimodally-acting mu, delta or kappa opioid agonists, will markedly enhance the analgesic potency of said opioid agonist, and render said opioid agonist comparable in potency to etorphine or dihydroetorphine, which, when used alone at higher doses, are >1000 times more potent than morphine in eliciting analgesia.

Co-administration of one of these excitatory opioid receptor antagonists at low concentration (about $10^{-12}$M) during chronic treatment of sensory neurons with $10^{-6}$M morphine or other bimodally-acting opioids (>1 week in culture) prevented development of the opioid excitatory supersensitivity, including naloxone-precipitated APD-prolongation, as well as the tolerance to opioid inhibitory effects that generally occurs after chronic opioid exposure. This experimental paradigm was previously utilized by the inventors on sensory neurons in culture to demonstrate that co-administration of $10^{-7}$M cholera toxin-B subunit, which binds selectively to GM1 ganglioside and thereby blocks excitatory GM1-regulated opioid receptor-mediated effects, but not opioid inhibitory effects (see Shen and Crain, *Brain Res.*, Vol. 531, pp. 1–7 (1990)) during chronic opioid treatment prevents development of these plastic changes in neuronal sensitivity that are considered to be cellular manifestations related to opioid dependence/addiction and tolerance in vivo (see Shen and Crain, *Brain Res.*, Vol. 597, pp. 74–83 (1992)). Hence, according to this invention, the sustained use of a relatively low clinical dose of one of these selective excitatory opioid receptor antagonists, e.g., <1 microgram of etorphine, dihydroetorphine or diprenorphine, in combination with 10–100 micrograms of morphine or other conventional bimodally-acting opioid analgesics will result in analgesia comparable to that elicited by said analgesics when administered alone in milligram doses and will attenuate or even prevent development of physical dependence and other undesirable excitatory side-effects generally associated with said analgesics.

Estimates Of Specific In Vivo Dosages That Provide Improved Detoxification And Treatment Of Opiate Addicts Acute application of one of these excitatory opioid receptor antagonists, e.g., etorphine or dihydroetorphine, at a low concentration (about $10^{-12}$M) to chronic opioid-treated sensory neurons prevented the excitatory APD-prolonging effects precipitated by naloxone ($10^{-9}$M) (FIG. 5). The latter effects provide a novel cellular model to account for naloxone-evoked withdrawal supersensitivity in opiate addicts in vivo. The potent effects of etorphine and dihydroetorphine in blocking naloxone-evoked APD prolongation in chronic opioid-treated sensory neurons in vitro (FIG. 5) is due to their blockade of supersensitive excitatory opioid receptors which have become responsive to the weak agonist properties of naloxone. A similar mechanism may account for the efficacy of dihydroetorphine in suppressing naloxone-evoked withdrawal syndromes in opiate-addicted animals and humans (see Lange, *Toxicol. Applied Pharmacol.*, Vol. 54, pp. 177–186 (1992) and Qin, *Chinese J. Pharmacol. Toxicol.*, Vol. 6, (1992)). Hence, according to this invention, appropriately low doses of one of these selective excitatory opioid receptor antagonists, e.g., about 1 microgram in combination with a 10–1000 fold lower than standard dose of one of the opioids currently used for the treatment of opioid dependence, e.g., methadone, buprenorphine, will provide an improved method for detoxifying and weaning addicts from dependence on opiates.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for selectively enhancing the analgesic potency of a bimodally-acting opioid agonist selected from the group consisting of morphine, codeine, fentanyl, buprenorphine, methadone, enkephalin, dynorphin, and endorphin and simultaneously attenuating the undesirable excitatory side-effects caused by said bimodally-acting opioid agonist in a subject treated with said bimodally-acting opioid agonist comprising administering to the subject in combination with said bimodally-acting opioid agonist an amount of an excitatory opioid receptor antagonist selected from the group consisting of etorphine, dihydroetorphine and diprenorphine effective to enhance the analgesic potency of said bimodally-acting opioid agonist and attenuate the undesirable excitatory side-effects caused by said bimodally-acting opioid agonist.

2. The method of claim 1 wherein the undesirable excitatory side-effect is selected from the group consisting of anti-analgesic effects, physical dependence, tolerance, hyperexcitability and hyperalgesia.

3. The method of claim 1 wherein the dose of bimodally-acting opioid agonist to be administered is 10–1000 times less than the amount of that bimodally-acting opioid agonist which is typically administered clinically for analgesia.

4. The method of claim 1 wherein the dose of opioid receptor antagonist to be administered is 10–1000 times less than the dose of bimodally-acting opioid agonist administered.

5. The method of claim 1 wherein the mode of administration is selected from the group consisting of sublingual, intramuscular, subcutaneous and intraveneous.

6. A method for detoxifying and treating an opiate addict comprising administering to the opiate addict an analgesic amount of a bimodally-acting opioid agonist selected from the group consisting of methadone and buprenorphine in combination with an amount of an excitatory opioid receptor antagonist selected from the group consisting of etorphine, dihydroetorphine and diprenorphine effective to enhance the analgesic potency of said bimodally-acting opioid agonist and attenuate the undesirable excitatory side-effects caused by said bimodally-acting opioid agonist, thereby detoxifying and treating said opiate addict.

7. The method of claim 6 wherein the dose of bimodally-acting opioid agonist to be administered is 10–1000 times less than the amount of that bimodally-acting opioid agonist which is typically administered clinically for analgesia.

8. The method of claim 6 wherein the dose of opioid receptor antagonist to be administered is 10–1000 times less than the dose of bimodally-acting opioid agonist administered.

9. The method of claim 6 wherein the mode of administration is selected from the group consisting of sublingual, intramuscular, subcutaneous and intravenous.

10. A composition comprising an analgesic amount of a bimodally-acting opioid agonist selected from the group consisting of morphine, codeine, fentanyl, enkephalin, dynorphin, endorphin, methadone and buprenorphine and an amount of an excitatory opioid receptor antagonist selected from the group consisting of etorphine, dihydroetorphine and diprenorphine effective to enhance the analgesic potency of said bimodally-acting opioid agonist and attenuate undesirable excitatory side-effects caused by said bimodally-acting opioid agonist in a subject administered said composition.

* * * * *